United States Patent [19]

Jandrasits et al.

[11] Patent Number: 5,729,123
[45] Date of Patent: Mar. 17, 1998

[54] METHOD AND APPARATUS FOR PROBING RELATIVE VOLUME FRACTIONS

[75] Inventors: Walter G. Jandrasits, Pittsburgh; Thomas J. Kikta, Upper St. Clair, both of Pa.

[73] Assignee: The United States of America as represented by the United States Department of Energy, Washington, D.C.

[21] Appl. No.: 635,425

[22] Filed: Apr. 11, 1996

[51] Int. Cl.$^6$ ............................................. G01N 27/06
[52] U.S. Cl. .................. 324/71.1; 324/439; 324/693; 324/704; 73/19.1
[58] Field of Search ........................... 324/71.1, 439, 324/446, 642, 643, 664, 693, 694, 696, 697, 704; 73/19.01, 19.1, 61.41; 340/620

[56] References Cited

U.S. PATENT DOCUMENTS

| | | | |
|---|---|---|---|
| 4,786,857 | 11/1988 | Mohr et al. | 73/304 R |
| 5,043,706 | 8/1991 | Oliver | 73/19.1 X |
| 5,270,663 | 12/1993 | Sano et al. | 324/704 X |
| 5,412,326 | 5/1995 | Marrelli et al. | 324/643 |
| 5,554,936 | 9/1996 | Mohr | 324/642 |

*Primary Examiner*—Glenn W. Brown
*Attorney, Agent, or Firm*—Virginia B. Caress; William R. Moser; Paul A. Gottlieb

[57] ABSTRACT

A relative volume fraction probe particularly for use in a multiphase fluid system includes two parallel conductive paths defining therebetween a sample zone within the system. A generating unit generates time varying electrical signals which are inserted into one of the two parallel conductive paths. A time domain reflectometer receives the time varying electrical signals returned by the second of the two parallel conductive paths and, responsive thereto, outputs a curve of impedance versus distance. An analysis unit then calculates the area under the curve, subtracts the calculated area from an area produced when the sample zone consists entirely of material of a first fluid phase, and divides this calculated difference by the difference between an area produced when the sample zone consists entirely of material of the first fluid phase and an area produced when the sample zone consists entirely of material of a second fluid phase. The result is the volume fraction.

22 Claims, 5 Drawing Sheets

METHOD AND APPARATUS FOR PROBING RELATIVE VOLUME FRACTIONS

FIELD OF THE INVENTION

This invention generally relates to a method and apparatus for determining the instantaneous relative volume fractions of virtually any two-phase environment in which the two phases have differing dielectric properties.

DESCRIPTION OF THE RELATED ART

U.S. Pat. No. 4,786,857 to Mohr et al. discloses methods and systems for determining relative proportions of intermixed, non-homogeneous phases in a fluid, based on differing electrical permittivities. The probe transit time and/or average probe velocity provides a measure of the characteristics of the fluid. The measured quantity is then compared to predetermined values corresponding to relative proportions of the intermixed constituents, thus providing a measure of relative proportions. This technique requires numerous calibration curves at a variety of void concentrations in order for any degree of accuracy to be achieved.

The probe disclosed in the Mohr et al. patent consists of a central electrode coaxially surrounded by a second electrode. The second electrode has longitudinal slots extending therethrough in order to ensure communication with representative multiphase fluid conditions in the annular space between the first and second electrodes. The electrodes are connected to a time domain reflectometer. The electrodes are separate from any other parts of the system being monitored, that is, the probe is intrusive.

In general, prior art time domain reflectometry detection systems have failed to provide simple, direct methods or means for measuring void fractions over a continuous value range in a multi-phase environment. The prior art systems have also been intrusive, thus affecting the environment of the fluid of the system being monitored.

SUMMARY OF THE INVENTION

In accordance with the present invention, a method and apparatus are provided for measuring relative volume fractions which overcome the above-identified problems, as well as other problems of the prior art.

According to a preferred embodiment, a non-intrusive relative volume fraction probe for use in a multiphase fluid system includes first and second conductive paths defining therebetween and thereabout a sample zone within the multiphase fluid system, generating means for generating time varying electrical signals, means for injecting the time varying electrical signals into the first one of the parallel conductive paths, and a time domain reflectometer for first injecting the signal into the first conductive path and then receiving the time varying electrical signals returned by the second conductive path. The time domain reflectometer outputs a curve of impedance versus distance after receiving the returned signals. An analysis or calculator means then calculates the area under the curve, subtracts the calculated area from an area produced when the sample zone consists entirely of material of a first fluid phase, and divides this calculated difference by the difference between an area produced when the sample zone consists entirely of material of the first fluid phase and an area produced when the sample zone consists entirely of material of a second fluid phase. The result of the latter division is output as the relative volume fraction of the phase with the lower dielectric coefficient.

In accordance with a further aspect of the present invention, the two conductive paths of the probe are composed of separate conductors shorted together at two points to form a single non-overlapping circuit. In this advantageous embodiment, the separate conductors comprise adjacent heat exchange tubes that are already part of the multiphase fluid system being measured, thus this embodiment is non-intrusive. Preferably, input from the injecting device is located along the first conductive path halfway between these two points. Further, in this embodiment the signals are preferably returned from an adjacent point located along the second conductive path in order to maximize the intensity of the returned signal.

In another advantageous embodiment, the conductors comprise an internal conductor in the system and an external conductor adjacent to the internal conductor. The use of an external conductor makes this embodiment partially intrusive to the multi-phase fluid environment being measured. In one variation of this embodiment these separate conductors are shorted together only at one point with the signal injection and return paths connected to the opposite ends, respectively. In another variation of this partially intrusive embodiment, these separate conductors are shorted together at two points with input from the signal injecting device located half way between the two points.

In accordance with another embodiment of the present invention, the two conductive paths of the probe are formed from a single U-shaped conductor. This embodiment is fully intrusive to the multiphase fluid environment being measured.

Other objects, features and advantages of the invention will be set forth in or apparent from the detailed description of the preferred embodiments of the invention which follows.

BRIEF DESCRIPTION OF THE DRAWINGS

FIG. 5b illustrates the flow path seen by the current in the probe of FIG. 5a;

DETAILED DESCRIPTION OF THE PREFERRED EMBODIMENTS

Figure 1:
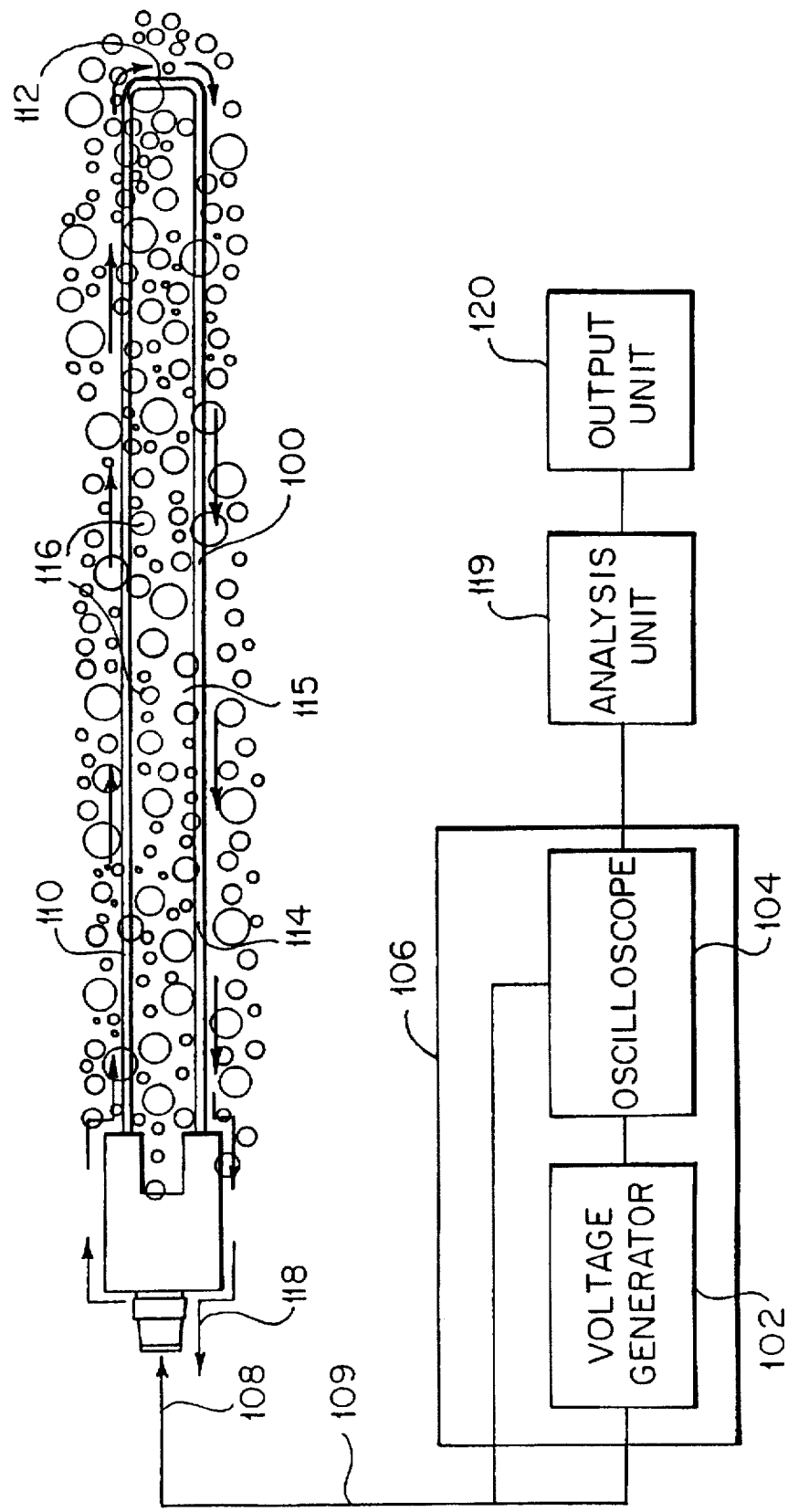
FIG. 1 shows a relative volume fraction probe assembly constructed in accordance with one embodiment of the present invention, as inserted in the media to be measured.

The present invention involves the provision of a relative volume fraction probe that is based on the measurement of the differences in dielectric properties between the phases of a two phase environment wherein the phases have differing dielectric properties. Although the discussion below will focus on void fractions, i.e. the relative volume fraction of a gas and/or vapor (gas/vapor) in a gas/vapor-liquid, it is to be understood the invention is not limited to such systems or environments and is, as stated, applicable to any environment wherein there is a significant difference in the dielectric properties of the phases. In essence, the relative volume fraction probe is or constitutes an electrical transmission line. The characteristics of this transmission line are readily determined using the principles of time domain reflectometry. Time domain reflectometers (TDRs) are readily available off the shelf from manufacturers such as Tektronix and Hewlett Packard, and a suitable TDR is, for example, the Tektronix 1502C metallic cable tester. Before considering FIG. 1, which shows a probe in the form of a transmission line 100 and the attendant circuitry of the system, reference is made to FIG. 2 which includes a diagram useful in understanding the characteristics of transmission line 100. As shown in FIG. 2, the transmission line 100 shown in the upper portion of FIG. 2 is modeled as an equivalent circuit of circuit elements 122 comprising a resistor R, conductance G, capacitor C and inductor L disposed, as illustrated, along and between the signal injection path 110 and the ground path 114 at any and every position x and, as will be appreciated, this is the equivalent circuit of actual transmission line 100 shown in the lower portion of FIG. 2 as inserted in a medium indicated at 115. In FIG. 2, the medium is a two-phase dielectric medium with voids.

It will also be appreciated that the electric current wave induced or injected into transmission line 100 by a signal generator 102 (shown in FIG. 1) will require some finite time to travel to a point x down the line 100. As the current wave moves down the line 100, the phase of the voltage will lag behind the source voltage by an amount $\beta$. The phase shift is a function of the resistance, capacitance and inductance characteristics (represented by circuit elements 122) of the material of signal injection path 110, the material of ground path 114 and the media or environment 115 between these paths 110 and 114.

In the application thereof to the void fraction probe of the present invention, the characteristics of the signal injection path 110 and the ground path 114, as well as those of the connecting line or portion 112 of the U-shaped metal transmission line 100, will only change as a function of temperature. However, as the medium 115 between the metal conductor paths 110 and 114 changes from liquid to vapor phase, the capacitance (the major factor), the resistance and the inductance of this interstitial environment will also change. Therefore, the fluid changes in phase within the probe's domain of influence will be reflected by associated changes in the phase shift $\beta$.

The velocity of propagation $v_p$ of the voltage induced current wave down the transmission line 100 is a function of the step rise time $\tau$ and the phase shift $\beta$ of the current wave. This velocity of propagation $v_p$ approaches the speed of light $v_c$ in transmission lines with an air dielectric. In the general case where the medium 115 between the transmission line comprises an arbitrary material with a dielectric coefficient given by $e_r$, the velocity of propagation $v_p$ is simply the speed of light divided by the square root of a dielectric coefficient, i.e., $v_p = v_c / \sqrt{e_r}$.

The distance x the wave travels down the transmission line 100 in a given time t is solely determined by the velocity of propagation $v_p$.

The differences in the effective length of the transmission line 100 when immersed in different materials will thus vary as the ratio of the square root of their respective dielectric coefficients. For example, if the transmission line 100 is first immersed in air and then in water, its effective length should increase by:

$$\sqrt{e_r}\mid_{water}/\sqrt{e_r}\mid_{air} = \sqrt{56}/\sqrt{1} = 7.48.$$

Therefore, in the application thereof to the void fraction probe of the present invention, the effective length of the probe changes as a direct function of the instantaneous dielectric coefficient of the medium between the signal injection and the ground paths of the void fraction probe.

The voltage will also be attenuated by an amount $\alpha$ by the series resistance R and the shunt conductance G of the line. The phase shift $\beta$ and the attenuation constant $\alpha$ combine to define the propagation constant $\gamma = \alpha + j\beta$. The propagation constant $\gamma$ may be used to define the voltage $E_x$ and the current $I_x$ in terms of the input magnitudes $E_{in}$, $I_{in}$ at any location x along a transmission line, as follows:

$$E_x = E_{in} e^{-\gamma x}$$

$$I_x = I_{in} e^{-\gamma x}.$$

At any point x along the line, the voltage and current are related by the characteristic impedance of the line $Z_o = E_x/I_x = E_{in}e^{-\gamma x}/I_{in}e^{-\gamma x}$. When a transmission line of finite length is terminated by a load with an impedance that matches the characteristic impedance of the line, then the governing voltage and current relationships are precisely those given above. When the load impedance $Z_L$ is different from the characteristic line impedance $Z_o$, the equations given above are not descriptive of the voltage and current relationships unless a second wave is superimposed on the incident wave. This reflected wave is energy that is not delivered to the load and is considered to originate at the load and propagate back in the line towards the source. Thus, the vertical amplitude of the return signal is also a function of the instantaneous dielectric coefficient of the medium between the signal injection path 110 and ground path 114 of the probe.

In the application thereof to the void fraction probe, interpretation of these relationships becomes somewhat more complex. While a short circuit load impedance $Z_L$ may be considered to be independent of any influences resulting from changes in the dielectric coefficient, the characteristic impedance and the transmission line $Z_o$ changes continuously. This is because the line's capacitance, inductance and conductance depend directly on the dielectric coefficient, which is changing as different voids pass by.

Figure 3:
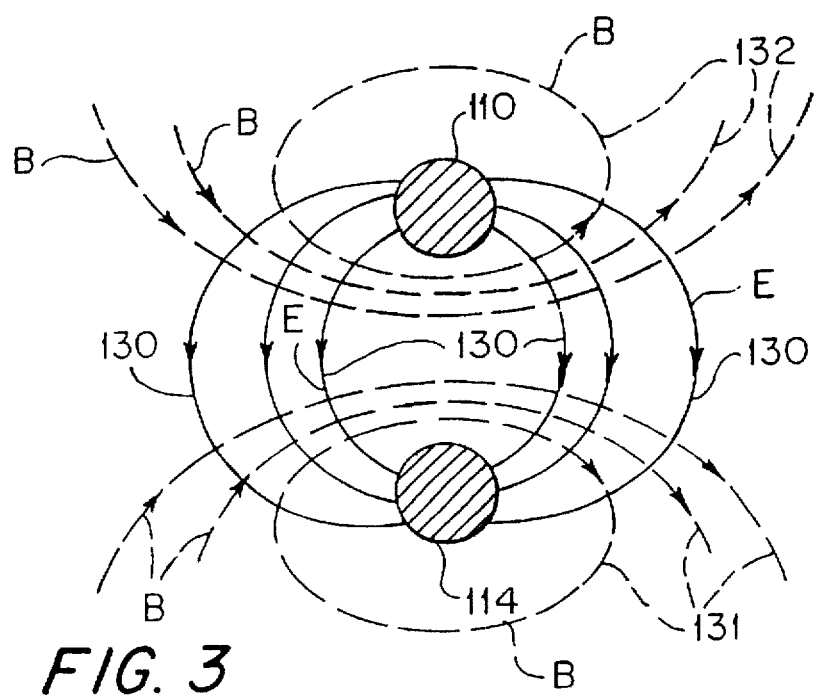
FIG. 3 illustrates the electric (E) and magnetic (B) equipotential field lines of the conductors of FIG. 1 and FIG. 2.

By ascertaining the relationships between the physics of electromagnetic theory and the geometric configuration of a transmission line the following can be shown. A high frequency electric current wave will travel on the surface of the conducting medium. Any form of conducting media functions as a transmission line, providing there is a positive (+) charge conductor and a negative (−) charge conductor. For pairs of conductors, the capacitance per unit length formed by the conductors is a function of the dielectric constant of the medium, $K = K_r K_o$. Further, as shown in FIG. 3 for a pair of circular conductors, the strength or magnitude of the equipotential fields, E and B, is a function of the dielectric constant in the medium K. For pairs of circular conductors, the electric (E) and magnetic (B) equipotential field lines denoted 130, and 131 and 132, respectively are connected along and about a line connecting the centers of the conductor.

Exploiting these physical characteristics, a void fraction probe can be created using naturally occurring conductors. When both conductors of the probe are naturally occurring, the probe is non-intrusive. Injecting the high frequency alternating current wave onto the outside diameter of the first conductor and picking up the return signal on the corresponding point on the second conductor opposite the injection point provides a means to detect both the relative volume fractions passing between the two conductors, as well as any relative volume fraction changes caused by the phases contacting the conductors. Additionally, because only the signal injection/return wire ends need to be appropriately spot-welded to the probe tubes, the tube bundle fabrication is simple.

Figure 2:
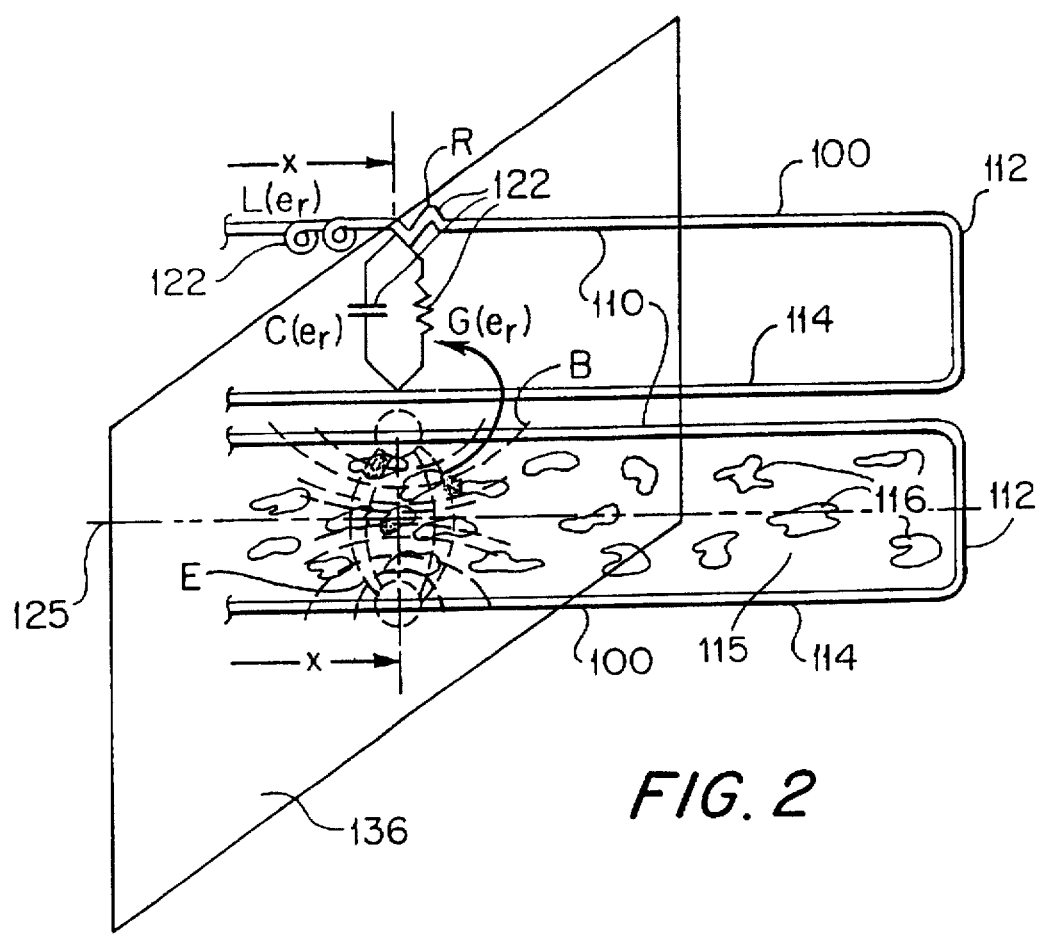
FIG. 2 shows the U-shaped conductor of the probe of FIG. 1, as inserted in the media to be measured in the lower portion of FIG. 2, and the equivalent circuit of this configuration in the upper portion of FIG. 2, with a distance indicating the cutting plane therebetween.

In an embodiment exploiting the above advantages, the void fraction probe comprises, in its most simple form shown in FIG. 1, the aforementioned transmission line 100 fabricated as a U-shaped wire and having the ends thereof connected to a time domain reflectometer 106. The connecting link portion or U-end 112 of the line 100 is a direct short between the signal insertion path 110 and the ground path 114 of the transmission line 100. To measure the void fraction, this wire only needs to be placed in a two phase environment, and oriented such that the two phase medium, passes between the straight legs 110 and 114 of the U-shape. In other words, maximum sensitivity to changes in the relative volume fraction is achieved when the flow is normal to the plane of the probe. The two phase medium is again indicated generally at 115 in FIG. 1, with the voids being generally indicated at 116.

As shown in FIG. 1, a TDR meter 106 connected to the transmission line 100 displays the impedance characteristics of transmission line 100 on a gated oscilloscope 104, thereby, in general application, indicating where along the path the characteristics of the transmission line 100 have changed or identifying which component of the transmission line has mismatched or failed characteristics. The TDR 106 uses a fast rise time ($\tau \leq 200$ picoseconds) voltage generator 102 and the oscilloscope 104 to form a system that acts like a wire directed radar directed along the transmission line 100.

A cable (e.g. a coaxial cable) 109 connects the input end 108 and an input/output end 118 of line 100 to the voltage generator 102 and gated oscilloscope 104 constituting the time domain reflectometer 106. The voltage generator 102, which preferably comprises a fast rise time voltage step generator, induces an electric current wave that is propagated down the transmission line 100, and the oscilloscope 104 monitors the incident and reflected waves along the line 100.

The horizontal axis of the oscilloscope 104 maps positions x along the line as a function of the step propagation velocity $v_p$, and the vertical axis maps the impedance $Z_o$ as a function of the voltage $E_x$ and current $I_x$ at positions x. Thus, the shape of the display on the oscilloscope 104 reveals the characteristic impedance of the transmission line 100, displaying both (i) the locations and (ii) the resistive, capacitive or inductive characteristics of the conductive discontinuities along the line.

The change in dielectric coefficient is caused by the changing fluid phase characteristics and is displayed on the oscilloscope 104 as a change in the horizontal magnitude of the return signal. The firmware in the oscilloscope 104 converts the time required by the wave to propagate to any given point into the distance x that the point is located from the origin of the transmission line. Therefore, the horizontal axis on the TDR oscilloscope 104 represents distance, not time.

A computer or analysis unit 119 connected to the output of TDR 106 can be programmed to automatically record and analyze data from the TDR. The information is used to give a reliable indication of the void fraction existing within the medium in which the probe is inserted, as will be explained in more detail hereinafter. The computer 119 is preferably provided with an output unit 120 in the form of a visual display or other suitable data output or interface device, as is conventional in the art.

Each point on the TDR meter curve is the measure of the characteristic impedance $Z_o$ between the signal injection and ground paths 110 and 114 at position x. The capacitance C, the inductance L and the conductance G are functions of the instantaneous dielectric coefficient $e_r$ of the medium between the two paths 110 and 114 at the point x. Each point on the curve displayed on the TDR meter 106 is actually an area function containing void fraction type information. Each point represents data that is mapped from the finite planar area that results from the outer section of a cutting plane 136 shown in FIG. 2 and the fluid domain beyond the two paths 110 and 114 of the probe, at a given location x along the probe, as shown in FIG. 2.

The finite planar area referred to above is bounded left and right by the surfaces of the signal and ground paths 110 and 114, the top and bottom by the natural extremes of the electromagnetic lines and the influence between the probe paths, i.e., the plane that is illustrated in FIG. 3. At any given point in time, this area has a property that appears like, but is not equal to, the first derivative of the instantaneous void volume with respect to the probe's axial coordinate variable. The corresponding area of the probe is indicated at 125 in FIG. 2 for the actual probe. The area in question is offset from the first derivative by the amount of volume associated with a 100% void phase. Therefore, in order to obtain actual void fraction information, it is necessary to generate a finite volume by sweeping these areas over the effective length of the probe, or the equivalent.

The thermodynamic definition of void fraction dictates that the void distribution is uniformly "smeared" throughout the control volume. When the void fraction is viewed through using TDR 106, there is a statistically significant finite probability that, under a non-zero void fraction operating condition, one or more 100% liquid data traces, which correspond to zero void fraction, will be collected. This is because at any given time, the portion of a void 116 that penetrates and remains present in the probe's control volume is totally controlled by the void phase velocity and the mean distance between voids. Therefore, even under steady state operating conditions, the physical development of the thermodynamic pseudo-property, void fraction, is a complex function of time involving void phase velocity, void formation rate, and void phase separation rate. Accordingly, assuming a negligible mean distance between voids, in the direction of flow, the minimum amount of time, $t_{min}$, for which consecutive data traces must be collected in average is calculated by: $t_{min}$=(height of probe's control volume)/ (average void phase velocity).

Figure 4A:
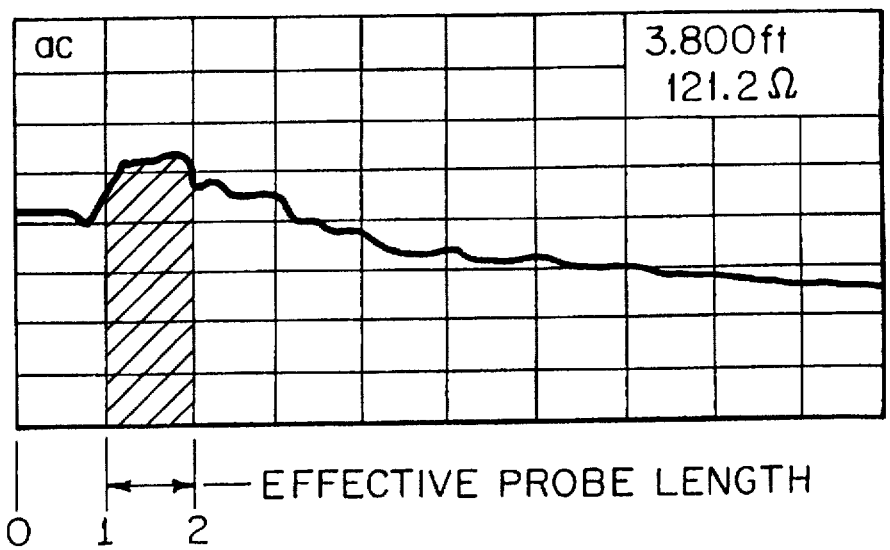
FIG. 4a is a plot of the impedance versus distance when the media within the probe of FIG. 1 is all air.
Figure 4B:
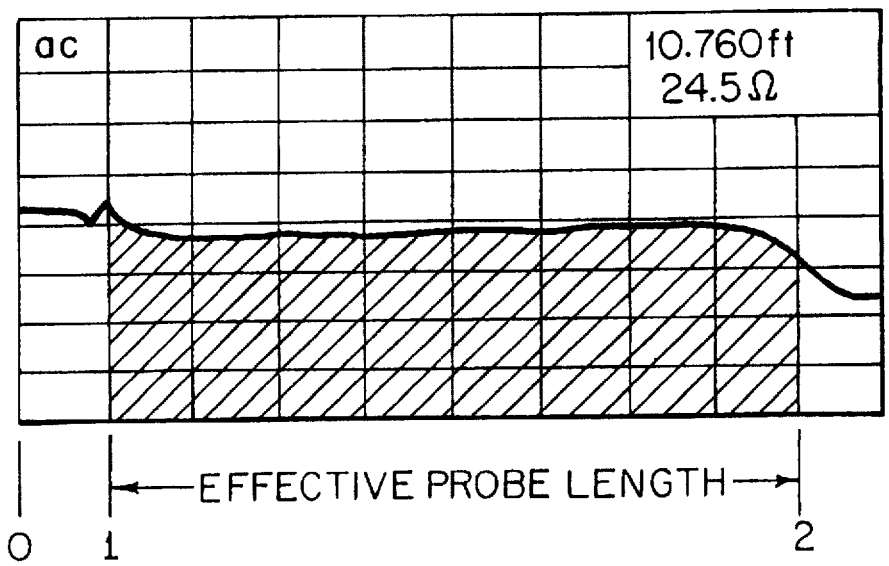
FIG. 4b is a plot of the impedance versus distance when the media within the probe of FIG. 1 is all water.

A two point calibration at a given temperature is used to define the void fraction in the present invention. The void fraction is defined as being equal to zero for the portion of the TDR meter display for 100% liquid, shown in FIG. 4b. The void fraction is defined as being equal to one for the appropriate portion of the TDR display meter for a 100% gas/vapor, shown in FIG. 4a. Note that, as discussed above, the effective length for the transmission line in water, shown in FIG. 4b, is roughly seven and a half times longer than the length in air, shown in FIG. 4a. The variation or change associated with void fractions between these two limits is assumed to be linear. Therefore, the two calibration curves shown in FIGS. 4a and 4b encompass all possible combinations of void fraction at each position x along the probe.

Generally, the area under the TDR meter curve (plotting impedance $Z_o$ versus distance x) associated with a liquid medium between the signal injection and ground paths 110 and 114 will be greater than the area associated with a gas/vapor medium. To obtain the total volume, the area under the 100% gas/vapor calibration curve is subtracted from the area under the 100% liquid calibration curve in analyzing unit 119. This total volume represents the total volumetric region or domain of interest where the probe can detect voids and identify the domain to be 100% full of voids, i.e., it is the TDR mapped form of the total control volume of the probe. To obtain the instantaneous void volume, the analyzing unit 119 subtracts the area under the desired operating condition data curve from the 100% liquid data curve. The analyzing unit 119 then computes the void fraction, VF, which is defined as VF =(instantaneous void volume)/(total volume).

Figure 5A:
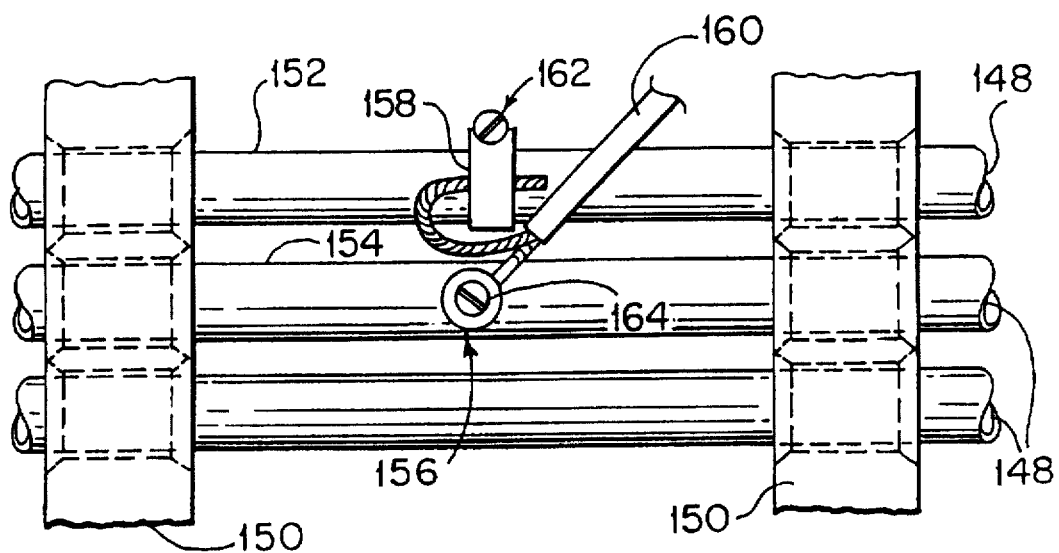
FIG. 5a illustrates another embodiment of the void fraction probe of the present invention.
Figure 5B:
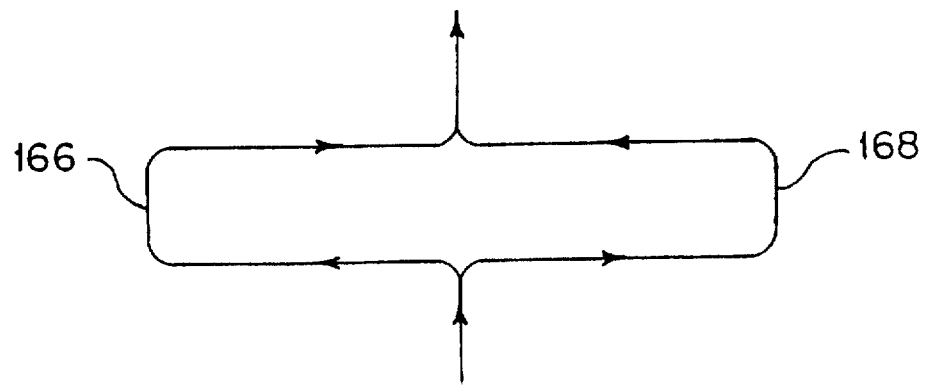

An alternative, presently preferred embodiment or configuration to the U-shaped conductor is shown, by example, in FIGS. 5a and 5b. In this example, parallel conductors 152 and 154 comprising two of a plurality of conductors 148 are electrically connected at each end by the component support structures 150. The support structures 150 are made of a conducting material, preferably a metal, and are spaced apart (a twelve inch separation performed well in the demonstrative embodiment). The transmission line of the void fraction probe consists of the two conductors 152 and 154. The length of the probe is controlled by the position of the support structures 150, i.e., the span of the conductors that are shorted together at the support structures 150 to thus form a parallel probe.

The electric current wave propagating down the coaxial cable can be injected into the conductors 152 and 154 anywhere between the support structures 150. As shown in FIG. 5b, when the wave recognizes that there are two paths, the wave will split proportionately to the impedance of each path forming a U-shaped path to the left indicated at 166 and a U-shaped path to the right indicated at 168. In order to simultaneously balance and maximize the sensitivity of the left and right probes of the probe within the capabilities of the TDR meter for this application, as shown in FIG. 5a, a signal injection tap or point 156 and a ground injection tap 158 are provided at the ends of a coaxial cable 160 and placed directly in the middle of the span of the conductors 152 and 154 as defined by the support structures 150. The coaxial cable 160 is preferably connected to the signal injection point 156 and ground injection point 158 by welding or brazing. However, in the demonstrative embodiment, FIG. 5a, the coaxial cable 160 is connected to the signal injection point 156 using a nylon screw 164 and to the ground injection point 158 using a hose clamp 162.

The TDR meter impedance versus distance curve, for equal distances to the left and to the right of the signal injection tap point 156, overlap on the meter display, i.e., the TDR meter cannot distinguish between the signal contributions from the left side U-probe and the right side U-probe for corresponding equivalent overlapping lengths. Thus, the signals from each side are simply combined as if the two U-shaped probes were folded over on top of each other about the base of each of the Us.

Because support structures 150 naturally occur, i.e., are part of the component being monitored, it is possible to exploit the usual, existing configuration of almost any system as a transmission line. In the alternative to natural support structures 150, artificial bounds may be used to short circuit the two conductors anywhere along the length of the conductors in order to optimize the sensitivity of the probe. The coaxial cable would then be attached midway to the created span. This allows the probe of the present invention to be placed anywhere that is desired and the length of the span is only limited by the resolution of the TDR meter 106.

Alternatively, one of the parallel conductors in FIG. 5a may be an external, non-naturally occurring conductor that is electrically connected at the desired span length ends by a shorting connection.

Figure 6A:
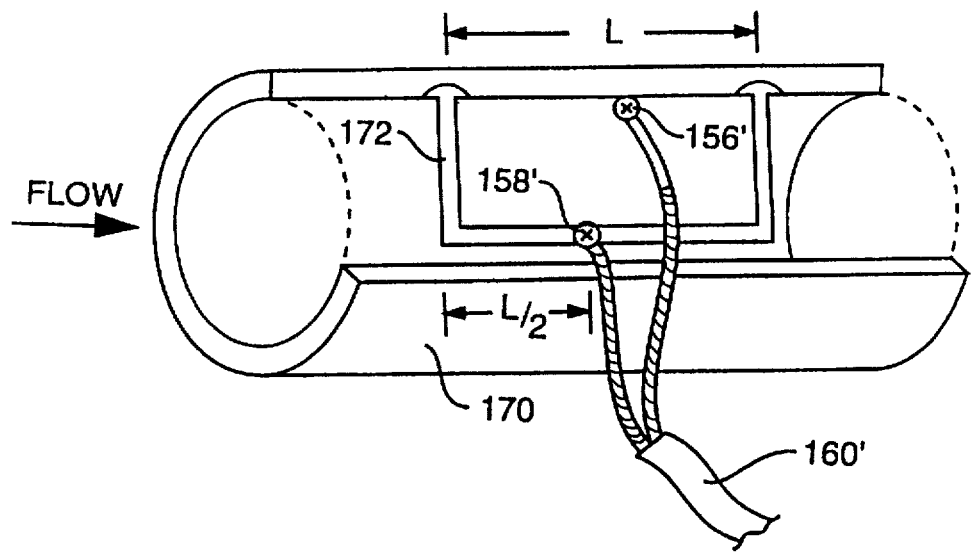
FIG. 6a illustrates a further embodiment of the invention which provides mid-point injection.

Two embodiments corresponding to two alternative implementations discussed above are illustrated in FIGS. 6a and 6b. In FIG. 6a, which is an example of a partially intrusive probe with mid-probe signal injection, a pipe 170 is shown in partial section for purposes of clarity. The pipe 170 constitutes the naturally occurring fluid control surface (internal conductor) while the external conductor has to be introduced to provide the signal return path as well as to define the fluid region of interest interrogated by the probe, i.e., the sample zone. In the embodiment of FIG. 6a, a conductor 172, having a length L, is introduced which comprises a U-shaped element shorted at both ends to the internal surface of pipe 170, as illustrated. In this embodiment, the conductors or leads of a coaxial cable 160' are connected to an injection point 156' located on the internal surface of pipe 170 and to a return point 158' located at the mid-point (L/2) of the external conductor 172 so as to provide the mid-point signal injection.

Figure 6B:
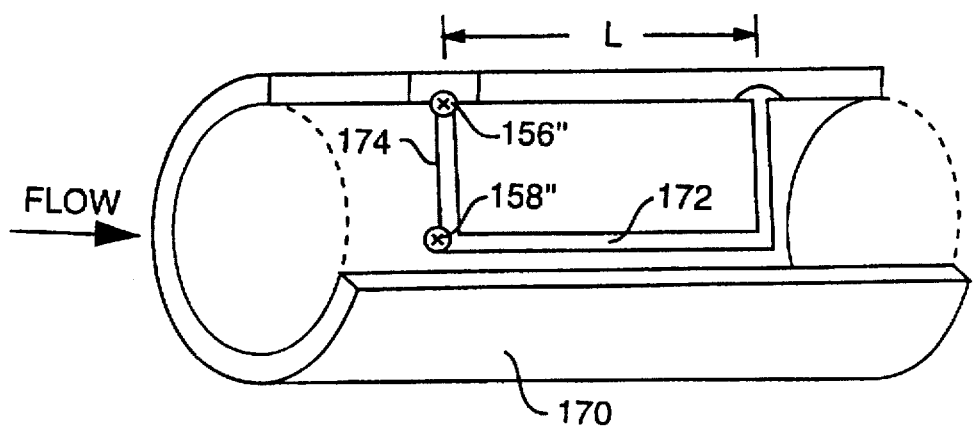
FIG. 6b illustrates yet another embodiment of the invention which is similar to FIG. 6a and which provides end-probe injection.

Referring to FIG. 6b, an embodiment similar to FIG. 6a is shown which provides end-probe signal injection. In this embodiment, the "external" conductor 172 is shorted to the internal surface of pipe 170 only at one end while the other end is supported by non-conductive support 174. The injection point 156" is provided at the internal surface of pipe 170 and the return point 158" is provided at the end of the external conductor 172 supported by non-conductive support 174. The coaxial connections of FIG. 6a are omitted in FIG. 6b for purposes of clarity and simplicity.

The technique of the invention is applicable to other conductor geometries, such as concentric conductors, given the space or form of the potential field associated with the transmission line. In this case, the electric field lines E will be radially directed straight lines between the inner and outer cylinders, like spokes on a wheel. Since the E and B fields are mutual orthogonal fields, the magnetic field lines B are a family of concentric circles between the inner and outer cylinders.

Although the present invention has been described relative to specific exemplary embodiments thereof, it will be understood by those skilled in the art that variations and modifications can be affected in the exemplary embodiments without departing from the scope and spirit of the invention.

What is claimed is:

1. A relative volume fraction probe assembly for use in a multiphase system comprising first and second phases having significantly different dielectric properties, said probe comprising:

first and second conductive paths defining therebetween a sample zone within the multiphase system;

generating means for generating a time varying electrical signals;

injecting means for injecting said time varying electrical signals into said first conductive path;

a time domain reflectometer for receiving said time varying electrical signals returned by said second conductive path and for producing a curve of impedance versus distance in response thereto; and calculating means for calculating the area under said curve, for subtracting the calculated area from an area produced when said sample zone consists entirely of material of the first phase so as to produce an area difference value, and for dividing said area difference value by the difference between a curve area produced when said sample zone consists entirely of material of said first phase and a curve area produced when said sample zone consists entirely of material of the second phase to thereby produce the relative volume fraction.

2. A relative volume fraction probe as recited in claim 1, wherein said conductive paths comprise two adjacent heat exchange tubes, and said probe is non-intrusive.

3. A relative volume fraction probe as recited in claim 1, wherein said two conductive paths comprise an internal conductor of the multiphase fluid system and an external conductor disposed adjacent to said internal conductor.

4. A relative volume fraction probe as recited in claim 3, wherein said probe is partially intrusive and said internal and external conductors comprise separate conductors shorted together at two points.

5. A relative volume fraction probe as recited in claim 3, wherein said probe is partially intrusive and said conductors are shorted together at one end point.

6. A relative volume fraction probe as recited in claim 5, wherein said injecting means is located along said first conducting path at an end thereof opposite said shorted end.

7. A relative volume fraction probe as recited in claim 5, wherein said time varying electrical signals are returned from said second conductive path at one end thereof opposite said shorted end.

8. A relative volume fraction probe as recited in claim 3 wherein said internal conductor comprises an inside surface of a pipe.

9. A relative volume fraction probe as recited in claim 1, wherein said probe is fully intrusive and said two conductive paths are formed from a single U-shaped conductor comprising a pair of conductor legs interconnected by a base conductor constituting a shorted end of said probe.

10. A relative volume fraction probe as recited in claim 9, wherein said injecting means is located along said first conducting path at an end thereof opposite said shorted end.

11. A relative volume fraction probe as recited in claim 9, wherein said time varying electrical signals are returned from said second conductive path at an one end thereof opposite said shorted end.

12. A relative volume fraction probe as recited in claim 1, wherein said two conductive paths comprise separate conductors shorted together at two points.

13. A relative volume fraction probe as recited in claim 12, wherein said injecting means is located along said first conductive path halfway between said two points.

14. A relative volume fraction probe as recited in claim 12, wherein said time varying electrical signals are returned from said second conductive path halfway between said two points.

15. A method for determining the relative volume fraction in a multiphase system comprising first and second phases having significantly different dielectric properties, said method comprising the steps of:

defining a sample zone within the multiphase system between first and second conductive paths;

generating time varying electrical signals;

injecting said time varying electrical signals into said first conductive path;

receiving said time varying electrical signals returned by said second conductive path and outputting a curve of impedance versus distance in response thereto;

calculating the area under said curve to produce a calculated area;

subtracting said calculated area from an area produced when said sample zone consists entirely of material of the first phase so as to produce an area difference value;

dividing said area difference value by the difference between a curve area produced when said sample zone consists entirely of material of said first phase and a curve area produced when said sample zone consists entirely of material of said second phase; and outputting the result of the dividing step as the relative volume fraction.

16. A method as recited in claim 15, wherein the defining step comprises providing a short circuit path between a conductor external to the multiphase system and an internal conductor in the multiphase system.

17. A method as recited in claim 15, wherein said defining step comprises shorting together said first and second conductive paths at two points.

18. A method as recited in claim 17, wherein said receiving step comprises returning said time varying electrical signals from a point along said second conductive path located halfway between said two points.

19. A method as recited in claim 17, wherein said injecting step comprises injecting said time varying electrical signals at a point along said first conductive path halfway between said two points.

20. A method as recited in claim 15, wherein said defining step comprises shorting together said first and second conductive paths at one end point.

21. A method as recited in claim 20, wherein said injecting step comprises injecting said time varying electrical signals at a point along said conductive path at an end thereof opposite said shorted end.

22. A method as recited in claim 20, wherein said receiving step comprises returning said time varying electrical signals from a point along said second conductive path located at an end thereof opposite said shorted end.

* * * * *